(12) United States Patent
Chiang et al.

(10) Patent No.: US 8,481,095 B2
(45) Date of Patent: Jul. 9, 2013

(54) METHOD FOR ANTI-OXIDATION, INHIBITING ACTIVITY AND/OR EXPRESSION OF MATRIX METALLOPROTEINASE, AND/OR INHIBITING PHOSPORYLATION OF MITOGEN-ACTIVATED PROTEIN KINASE USING FLEMINGIA MACROPHYLLA EXTRACT

(75) Inventors: Hsiu-Mei Chiang, Taichung (TW); Kuo-Ching Wen, Taichung (TW)

(73) Assignee: China Medical University, Taichung (TW)

( * ) Notice: Subject to any disclaimer, the term of this patent is extended or adjusted under 35 U.S.C. 154(b) by 206 days.

(21) Appl. No.: 13/034,370

(22) Filed: Feb. 24, 2011

(65) Prior Publication Data
US 2012/0164250 A1 Jun. 28, 2012

(30) Foreign Application Priority Data

Dec. 22, 2010 (TW) ................................ 99145269 A

(51) Int. Cl.
*A61K 36/00* (2006.01)
(52) U.S. Cl.
USPC .......................................... 424/779; 424/725
(58) Field of Classification Search
None
See application file for complete search history.

(56) References Cited

U.S. PATENT DOCUMENTS

2006/0003035 A1\* 1/2006 Majeed et al. ................ 424/773
2011/0082197 A1\* 4/2011 Wu et al. ....................... 514/456

FOREIGN PATENT DOCUMENTS

| CN | 1742795 | \* | 3/2006 |
| CN | 101167895 | \* | 4/2008 |
| CN | 101455814 | \* | 6/2009 |
| JP | 2000-247829 | \* | 12/2000 |
| JP | 2003-113031 | \* | 4/2003 |

OTHER PUBLICATIONS

Website publication entitled "AgroForestryTree Database". Obtained from http://www.worldagroforestrycentre.org. Downloaded from web on Dec. 30, 2012, 3 pages.\*
Syiem et al. Pharmacologyonline. 2009. vol. 3, pp. 952-965.\*
Shiao et al. Planta Med. 2005. vol. 71, pp. 835-840.\*
Rao et al. Phytochem. 1984. vol. 23, No. 4, pp. 927-929.\*
Kulkarni, A P. et al., In Vitro Studies on the Binding, Antioxidant, and Cytotoxic Actions of Punicalagin, Journal of Agricultural Food Chemistry, 2007, 55, 1491-1500.

\* cited by examiner

*Primary Examiner* — Chris R Tate
(74) *Attorney, Agent, or Firm* — Ping Wang; Andrews Kurth LLP

(57) ABSTRACT

A method for inhibiting at least one selected from the group consisting of oxidation, the activity of matrix metalloproteinase (MMP), the expression of matrix metalloproteinase, and the phosphorylation of mitogen-activated protein kinase (MAP kinase) in a mammal, comprising administrating to the mammal an effective amount of a *Flemingia macrophylla* extract.

17 Claims, 9 Drawing Sheets

METHOD FOR ANTI-OXIDATION, INHIBITING ACTIVITY AND/OR EXPRESSION OF MATRIX METALLOPROTEINASE, AND/OR INHIBITING PHOSPORYLATION OF MITOGEN-ACTIVATED PROTEIN KINASE USING FLEMINGIA MACROPHYLLA EXTRACT

This application claims the benefit of Taiwan Patent Application No. 099145269, filed on Dec. 22, 2010, in the Taiwan Intellectual Property Office, the disclosure of which is incorporated herein in its entirety by reference.

FIELD

The present invention relates to the uses of a *Flemingia macrophylla* extract in anti-oxidation, in the inhibition of the activity of matrix metalloproteinase (MMP), in the inhibition of the expression of matrix metalloproteinase, and/or in the inhibition of the phosphorylation of mitogen-activated protein kinase, especially in the improvement, care, and/or repair of skin.

BACKGROUND

Natural human aging processes include wrinkle formation, skin flaccidity and skin darkening, which gradually appear with aging. The layers of skin from top to bottom are the epidermis, dermis, and hypodermis. The causes of skin aging can be classified into endogenous and exogenous factors. Endogenous aging is a natural aging process of the human body, including cell apoptosis, hormone decrease, and weakened immunity. The decrease of hormone secretion may slow skin metabolism and gradually reduce the production of collagen and elastin due to the deterioration of fibroblast function in the dermis. As a result, the connective tissues in the dermis deteriorate, leading to skin flaccidity, and even wrinkling. Furthermore, the deterioration of the connective tissues in the dermis may decrease the water storage function of the skin, leading to skin dryness and water deficiency, etc.

Exogenous aging is caused by extrinsic factors, such as sunshine, pollution, free radicals, and smoking. The factor that damages the skin most and accelerates the aging of skin is ultraviolet (UV) rays from the sun. Based on the wavelength, ultraviolet (UV) rays can be classified into long wavelength UV (UVA), medium wavelength UV (UVB), and short wavelength UV (UVC). UV rays that people are most exposed to in daily life are UVA and UVB, which may cause erythema, sunburns, damage to the deoxyribonucleic acid (DNA) in skin cells, abnormality of the skin immune system, and skin cancer. The aging phenomenon caused by UV rays is called "photo-aging," which may increase the amount of matrix metalloproteinase (MMP) in the dermis via the phosphorylation of the mitogen-activated protein kinase (MAP Kinase) pathway. Matrix metalloproteinase may decompose collagen to reduce the collagen content in the skin. Furthermore, UV rays may promote the formation of reactive oxygen species (ROS), such as oxygen ions, peroxides, organic and inorganic radicals, etc, and cause denaturing of the collagen and loss of collagen function. Without the support of collagen, the skin becomes flaccid, and cuticula may overgrow, leading to darkened skin.

Currently known animal collagen can be classified approximately into 21 type, in which different kinds of collagen exist in different tissues. Out of all the collagen in skin tissue, Type I collagen is the most abundant (80% of skin collagen) and has the most functions. Type III collagen comprises about 20% of the skin collagen. Fibroblasts in the dermis mainly produce Type I collagen and Type III collagen for the skin.

As described above, matrix metalloproteinase may decompose collagen to reduce the collagen content in the skin, while reactive oxygen species will cause collagen to lose its function. Thus, if the oxidation reaction of the reactive oxygen species or the activity and/or expression of matrix metalloproteinase can be inhibited, then the effects of improving/caring for skin quality can be achieved.

It has been found that the expression of matrix metalloproteinase-1 can be inhibited by ziyuglycoside-I obtained by extracting the roots of *Sanguisorba officinalis* with 70% ethanol. The expression of matrix metalloproteinase-1 can also be inhibited by sumaflavone and amentoflavone obtained by extracting *Selaginella tamariscina* with methanol. However, there is still a need to find components that have better effects of inhibiting the activity of matrix metalloproteinase.

The inventors of the present invention discovered that a *Flemingia macrophylla* extract has excellent effects of anti-oxidation, inhibiting the activity of matrix metalloproteinase, inhibiting the expression of matrix metalloproteinase, and/or inhibiting the phosphorylation of mitogen-activated protein kinase. Thus, the extract can be used in the improvement, care, and/or repair of skin.

SUMMARY

The primary objective of this invention is to provide a method of inhibiting at least one selected from the group consisting of oxidation, the activity of matrix metalloproteinase (MMP), the expression of matrix metalloproteinase, and the phosphorylation of mitogen-activated protein kinase (MAP kinase) in a mammal, comprising administrating to the mammal an effective amount of a *Flemingia macrophylla* extract.

Another objective of this invention is to provide a *Flemingia macrophylla* extract, wherein the extract has a first absorption peak at a wavelength ranging from 255 to 290 nm. The extract preferably further has a second absorption peak at a wavelength ranging from 210 to 250 nm.

Yet a further objective of this invention is to provide a pharmaceutical composition for inhibiting at least one selected from the group consisting of oxidation, the activity of matrix metalloproteinase (MMP), the expression of matrix metalloproteinase, and the phosphorylation of mitogen-activated protein kinase, which comprises an effective amount of the aforesaid *Flemingia macrophylla* extract.

The detailed technology and preferred embodiments implemented for the subject invention are described in the following paragraphs accompanying the appended drawings for people skilled in this field to well appreciate the features of the claimed invention.

DESCRIPTION OF THE PREFERRED EMBODIMENT

Figure 1:
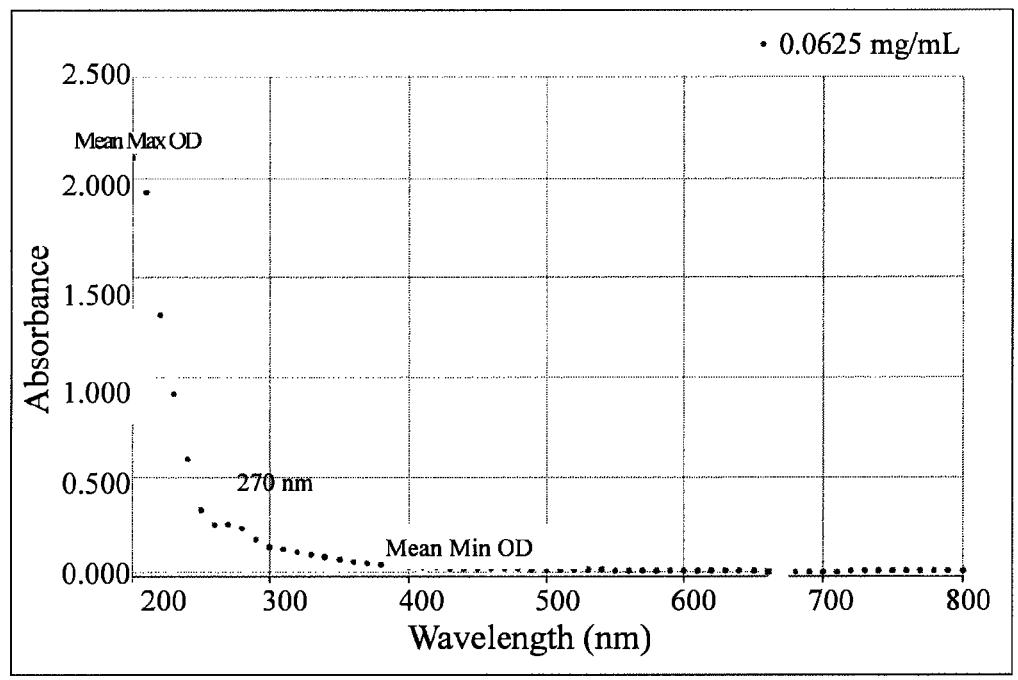
FIGS. 1 to 5 are UV-VIS spectrograms of the *Flemingia macrophylla* extract of the present invention.
Figure 2:
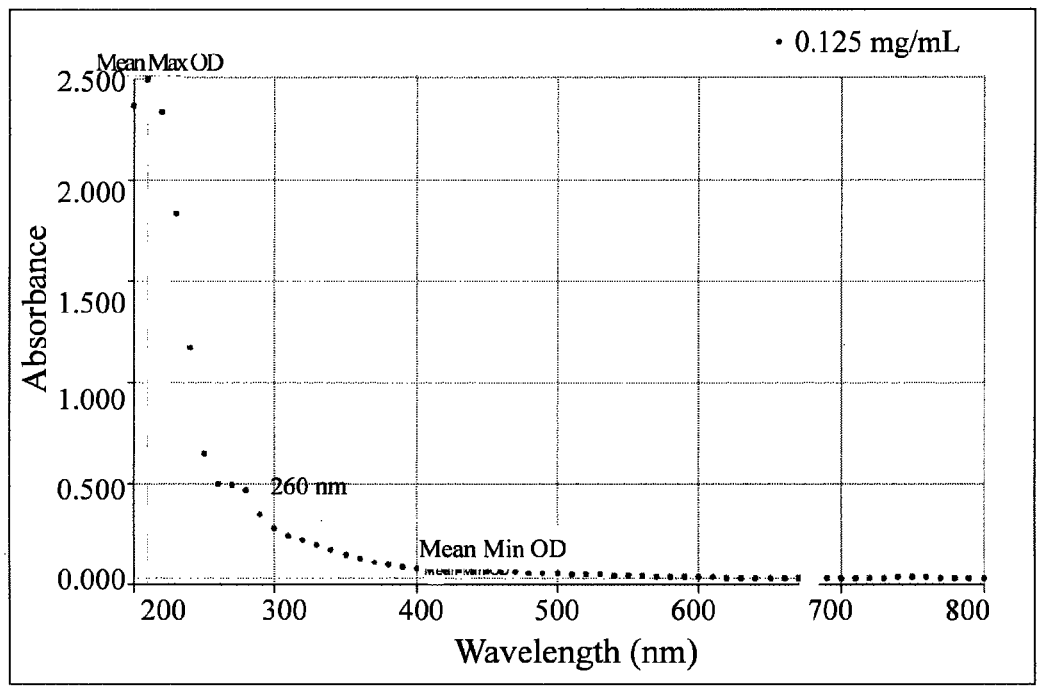
Figure 3:
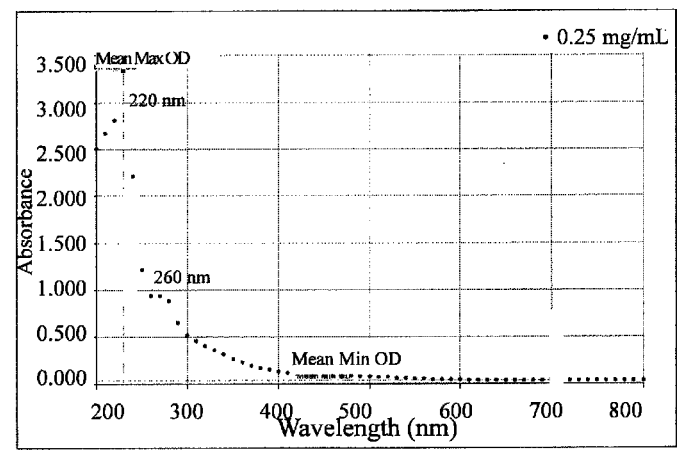
Figure 4:
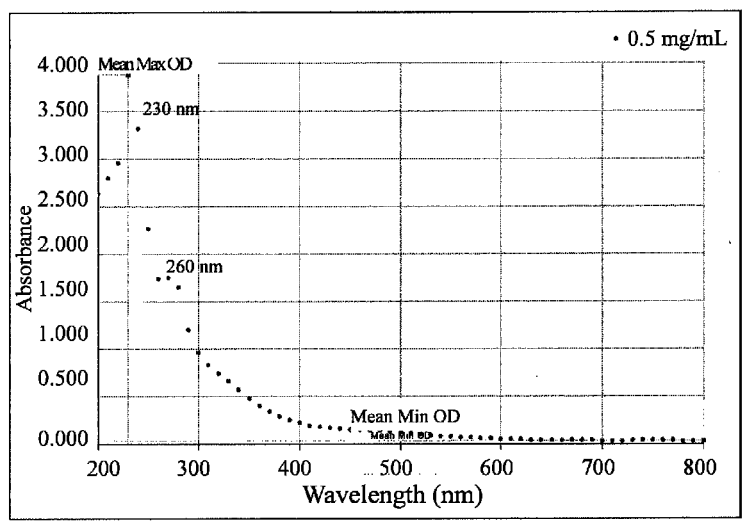
Figure 5:
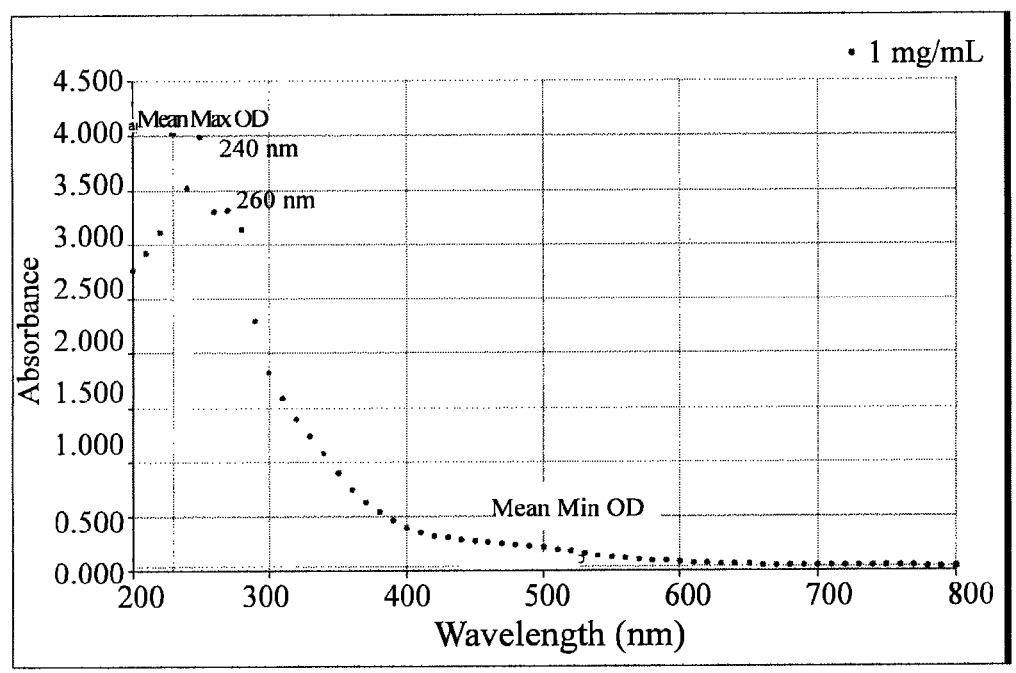

Unless otherwise stated herein, the terms "a (an)", "the" or the like used in this specification (especially in the claims hereinafter) shall be understood to encompass both the singular and plural forms.

The present invention relates to a method of inhibiting at least one selected from the group consisting of oxidation, the activity of matrix metalloproteinase (MMP), the expression of matrix metalloproteinase, and the phosphorylation of mitogen-activated protein kinase (MAP kinase) in a mammal, comprising administrating to the mammal an effective amount of a *Flemingia macrophylla* extract. The absorption spectroscopy of the *Flemingia macrophylla* extract has a first absorption peak at a wavelength ranging from 255 to 290 nm. The extract preferably further has a second absorption peak at a wavelength ranging from 210 to 250 nm. In one embodiment, the absorption spectroscopy of the *Flemingia macrophylla* extract includes peaks within the following wavelength ranges: from 215 to 245 nm and from 255 to 280 nm.

The inventors of the present invention discovered that the *Flemingia macrophylla* extract of the present invention has the effects of inhibiting the activity of matrix metalloproteinase and inhibiting the expression of matrix metalloproteinase, and may prevent or decrease the destruction of collagen. Matrix metalloproteinase can be classified as collagenase, stromelysin, gelatinase, matrilysin, transmembrane type-MMP, etc. In particular, the *Flemingia macrophylla* extract of the present invention can effectively inhibit the formation (or expression) of matrix metalloproteinase-1 (MMP-1), matrix metalloproteinase-3 (MMP-3), and matrix metalloproteinase-9 (MMP-9). MMP-1 is also called collagenase-1, which belongs to the collagenase family. Other names for MMP-1 include tissue collagenase or fibroblast-type collagenase. MMP-3 is also called stromelysin-1, which belongs to the stromelysin family, and substrates of which include fibronectin, laminin, and non-fibrillar collagen. MMP-9 belongs to the gelatinase family, a major substrate of which is Type IV collagen. Without being limited by theory, it is believed that the *Flemingia macrophylla* extract of the present invention can indirectly increase the formation of collagen by inhibiting the activity and/or expression of matrix metalloproteinase.

Apart from effectively inhibiting the activity and/or expression of matrix metalloproteinase, the extract of the present invention also can inhibit the phosphorylation of mitogen-activated protein kinase (MAP kinase), in particular, it can inhibit the phosphorylation of c-Jun N-terminal Kinase (JNK), the extracellular signal-regulated protein kinase (ERK), and p38 protein. As stated above, the phosphorylation of MAP kinase would increase the amount of matrix metalloproteinase in the dermis, therefore increasing the opportunity of collagen degradation and decreasing the collagen content in skin.

In addition, the *Flemingia macrophylla* extract of the present invention also has anti-oxidation effects. As described above, the oxidation reaction of reactive oxygen species can denature collagen and cause it to lose its function, and thus collagen can no longer support the skin, leading to skin flaccidity and darkening. Compared with the conventional method that isolated punicalagin, a compound with anti-oxidation activity, from *Flemingia macrophylla*, the extract of the present invention has better applicability. Because of its cytotoxicity, punicalagin is not suitable for human or animal body (which can be seen in In Vitro Studies on the Binding, Antioxidant, and Cytotoxic Actions of Punicalagin, J. Agric. Food Chem., 2007, 55(4), 1491-1500, which is entirely incorporated hereinto by reference). However, as shown in the following examples, the extract of the present invention has no cytotoxicity, and therefore, is safer.

Because the *Flemingia macrophylla* extract of the present invention simultaneously has effects of (1) directly inhibiting the activity and/or expression of matrix metalloproteinase, (2) indirectly inhibiting the formation of matrix metalloproteinase by inhibiting the phosphorylation of mitogen-activated protein kinase, and (3) inhibiting the oxidation reaction of reactive oxygen species, it greatly reduces the collagen decomposition and denaturing in the skin, and may effectively improve, repair, and/or care for skin. For example, the extract may achieve effects of anti-aging, anti-photoaging, reducing skin wrinkles, improving skin quality and skin flaccidity, promoting wound healing, etc.

The *Flemingia macrophylla* extract of the present invention can be prepared by a method that comprises the following steps: a) extracting *Flemingia macrophylla* with a solvent and collecting the liquid phase; and optionally b) drying the collected liquid phase. The solvent (i.e., extraction solvent) that is commonly used is selected from a group consisting of water, alcohols, and combinations thereof. The solvent is preferably selected from a group consisting of water, $C_1$-$C_4$ alcohols, and combinations thereof. More preferably, the solvent is selected from a group consisting of water, methanol, ethanol, propanol, butanol, propylene glycol, and combinations thereof. Most preferably, the solvent is selected from a group consisting of water, methanol, and combinations thereof. The weight ratio of the extraction solvent and *Flemingia macrophylla* is not a key factor in the present invention, and is usually about 10:1 to about 30:1, and preferably about 15:1 to about 25:1.

Optionally, before step a), *Flemingia macrophylla* to be extracted is dried and ground to promote the effectiveness of the extraction. In step a), the extraction is carried out for a period of time to achieve the desired extraction efficiency. For example, when water is used as the extraction solvent, the extraction time is usually at least 20 minutes, more preferably at least 60 minutes, and most preferably at least 90 minutes. The extraction may be optionally assisted with other appropriate extracting approaches (e.g., ultrasonic vibration, heating, etc.) to increase extraction efficiency. In addition, prior to step b), the extraction in step a) may be optionally repeated one or more times, and all of the liquid phase are combined to provide a liquid phase for step b) to separate the active components from the inactive components in *Flemingia macrophylla* as much as possible to reduce resource waste and benefit the economy.

In general, depending on the application of the *Flemingia macrophylla* extract, a drying step may be optionally carried out to dry the *Flemingia macrophylla* extract liquid obtained in step a). For example, if the selected extraction solvent is methanol or ethanol, either of which is not irritating to the skin, and the obtained *Flemingia macrophylla* extract liquid is to be applied to the skin directly, additional drying for the extract liquid is not needed. However, if the *Flemingia macrophylla* extract of the present invention is to be applied by oral administration, a drying step (such as freeze drying, concentrating under a vacuum condition, and/or ventilation) can be used to remove the organic solvents in the *Flemingia macrophylla* extract to prevent the organic solvents from harming the body.

The extract of the present invention is preferably obtained by extracting the stems of *Flemingia macrophylla*. In one embodiment of the present invention, the finely ground powder of the stems of *Flemingia macrophylla* were extracted with water and soaked therein to obtain an extract liquid, and the weight ratio of water and the finely ground powder of the stems of *Flemingia macrophylla* was about 20:1. The extract liquid was then concentrated under a vacuum condition to obtain a dried *Flemingia macrophylla* extract.

The present invention also relates to a pharmaceutical composition for the anti-oxidation, inhibition of the activity of matrix metalloproteinase, inhibition of the expression of matrix metalloproteinase, and/or inhibition of the phosphorylation of mitogen-activated protein kinase, comprising an effective amount of the *Flemingia macrophylla* extract of the present invention. Specifically, the *Flemingia macrophylla* extract of the present invention can be administrated as a medicament. Because of the effects of the pharmaceutical composition of the present invention on the anti-oxidation, inhibition of the activity of matrix metalloproteinase, inhibition of the expression of matrix metalloproteinase, and/or inhibition of the phosphorylation of mitogen-activated protein kinase, the pharmaceutical composition can be particularly used for improving, repairing, and/or caring for the skin.

The pharmaceutical composition of the present invention can be of any suitable form without particular limits. For example, the pharmaceutical composition can be in the form of an emulsion, cream or gel for external use, such as a skin care product, cosmetic, etc. The pharmaceutical composition can also be prepared in the form of food for swallowing or drinking, such as health foods, beauty drinks, etc. Furthermore, the pharmaceutical composition can also be of a common pharmaceutical form, such as a tablet, a capsule, a granule, a powder, a fluid extract, a solution, a syrup, a suspension, an emulsion, a tincture, an intravenous injection, a powder injection, a suspension injection, and a powder-suspension injection, etc.

The content of the *Flemingia macrophylla* extract in the pharmaceutical composition of the present invention may be adjusted according to the age of the treated subject and the purpose of the application (such as reducing skin wrinkles or promoting wound healing). The usage frequency may also be optionally adjusted. For example, when the *Flemingia macrophylla* extract is used for reducing skin wrinkles, the content of the *Flemingia macrophylla* extract in the pharmaceutical composition usually ranges from about 0.03 wt % to about 0.4 wt %, and preferably ranges from about 0.05 wt % to about 0.25 wt %, based on the total weight of the pharmaceutical composition. The other components and content thereof are dependent on the final form of the pharmaceutical composition. For instance, when the pharmaceutical composition is prepared as a skin care product, any suitable and appropriate amount of emulsifying agent, perfume, and other active components for improving skin quality may be added therein. When the medicament is prepared as a tablet, an appropriate excipient can be used. In general, any component can be added to the pharmaceutical composition as long as it has no adverse influence on the desired effects of the *Flemingia macrophylla* extract.

The detailed technology and preferred embodiments implemented for the subject invention are described in the following paragraphs accompanying the appended drawings for people skilled in this field to well appreciate the features of the claimed invention. However, the scope of the present invention is not limited thereby.

[Preparation of the *Flemingia macrophylla* Extract]

*Flemingia macrophylla* illustrated in the following examples for the present invention was from Pingtung County, Taiwan. First, the dried stems of *Flemingia macrophylla* were ground and added into distilled water with a 20-fold weight corresponding to the weight of the stems. After being soaked for 30 minutes, the ground stems were boiled for 1 hour and then filtered to obtain a filtrate. Then, the filtrate was heated at 70° C. to 80° C. for 3 hours. Finally, the filtrate was freeze-dried to obtain the *Flemingia macrophylla* extract of the present invention.

The pH value of the *Flemingia macrophylla* extract of the present invention was about 5.45 in water (2 mg/ml). A UV-VIS Spectrophotometer (UV-160, Shimadzu) was used to detect the characteristic absorption wavelength of the extract. The UV-VIS absorption spectra are shown in FIGS. 1 to 5 (the concentration of the *Flemingia macrophylla* extract ranges from 0.0625 mg/mL to 1 mg/mL).

Example 1

Experiment A

Inhibition Test of Collagenase Activity

An agar gel (agar gel medium) was used in this experiment to evaluate the inhibition effect of the *Flemingia macrophylla* extract on collagenase.

In an eppendorf tube, 50 μL of a 10-fold diluted buffer solution (prepared by mixing 5 mL of 1 M Tris (pH 7.8), 1 mL of 1 M CaCl$_2$, 3.75 mL of 4 M NaCl, and 0.25 mL water), 30 μL of the distilled water, 10 μL (5 to 500 μg/mL) of the *Flemingia macrophylla* extract, and 10 μL of a bacterial collagenase (100 μg/mL, a multiple-functional collagenase obtained by gene recombination) were added and mixed evenly, and placed at room temperature for 1 hour. Then, the mixed solution (40 μL) was added onto a piece of filter paper on an agar gel medium and placed in an incubator at 37° C. to react for 18 hours. Afterwards, the filter paper was removed, and the medium was stained with a staining agent for 15 minutes, and then de-stained. A photograph of the medium was taken and analyzed by a TINA software (Prevx community, Germany) to calculate the inhibition rate of the *Flemingia macrophylla* extract. In the experiment, water and doxycycline were used to replace the *Flemingia macrophylla* extract as the control group and the positive control group, respectively, and the distilled water was used to replace collagenase for determining the background value. After the tests were independently carried out three times, the mean value and standard deviation were calculated with the following formula. The results are shown in Table 1 and FIG. 6.

$$\text{Inhibition Rate (\%)} = \left[\frac{(C-B)}{(A-B)}\right] \times 100$$

A: a solution comprising no collagenase and the extract

B: a solution comprising collagenase, but not the extract

C: a solution comprising collagenase and the extract

TABLE 1

| Group | distilled water | doxycycline (100 μg/mL) | extract (50 μg/mL) | extract (100 μg/mL) | extract (500 μg/mL) |
|---|---|---|---|---|---|
| Inhibition Rate (%) | −32.54 ± 27.6 | 100.3 ± 5.4 | 53.7 ± 7.2 | 79.5 ± 0.9 | 118.4 ± 7.9 |

Figure 6:
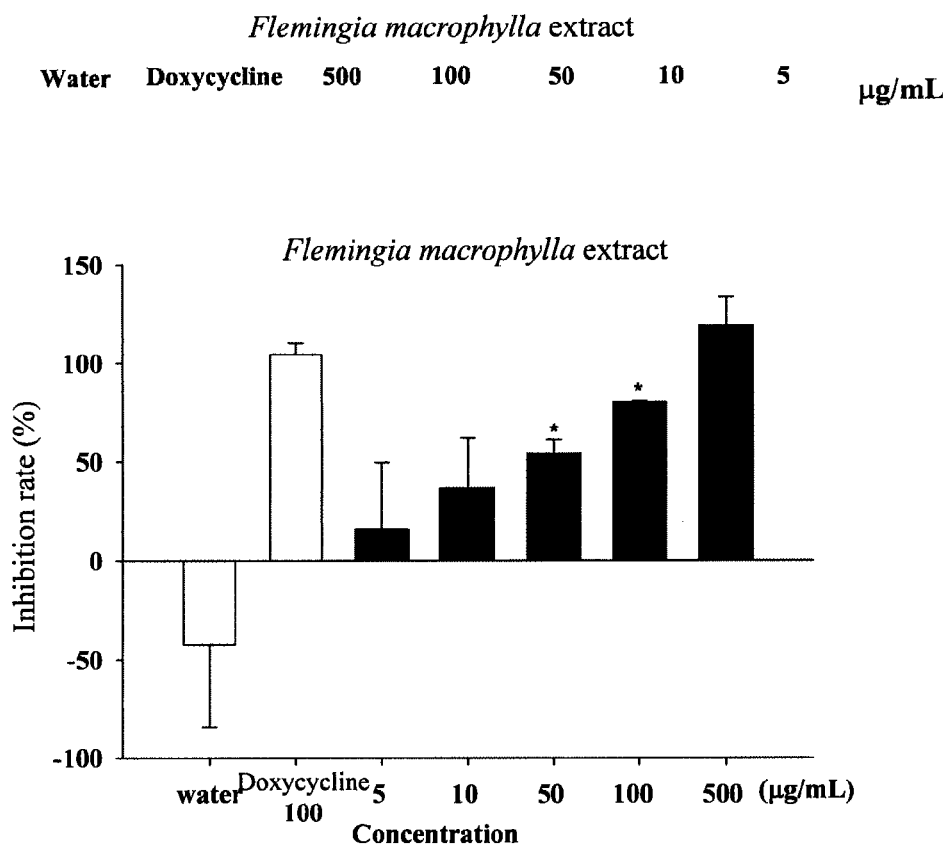
FIG. 6 is a bar diagram showing the inhibition rate of the *Flemingia macrophylla* extract of the present invention on collagenase.

As shown in Table 1 and FIG. 6, the inhibition rate of the doxycycline (100 μg/mL) in the positive control group was 100.3±5.4%; the inhibition rate of the distilled water in the control group was −32.54±27.6%; the inhibition rate of the *Flemingia macrophylla* extract (50 to 500 μg/mL) was 53.7±7.2%, 79.5±0.9%, and 118.4±7.9%, respectively. This test shows that the *Flemingia macrophylla* extract of the present invention can effectively inhibit the activity of collagenase.

Experiment B

Concentration-Dependent Inhibition Test of Collagenase Activity

To further confirm the inhibition effects of the *Flemingia macrophylla* extract on collagenase, the extract was diluted to various concentrations (10 to 500 μg/mL).

In an eppendorf tube, 132 μL of the distilled water, 22 μL of a 10-fold diluted buffer solution (prepared by mixing 5 mL of 1 M Tris (pH 7.8), 1 mL of 1 M CaCl$_2$, 3.75 mL of 4 M NaCl, and 0.25 mL water), 22 μL of the *Flemingia macrophylla* extract (10 to 500 μg/mL), 22 μL of a bacterial collagenase (100 μg/mL), and 22 μL of a fluorogenic substrate (fluorogenic peptide substrate I of collagenase) solution were added and mixed evenly, and placed in an incubator at 37° C. to react for 20 hours. Then, 200 μL of the reacted solution was placed into a 96-well microplate. The fluorescent strength of the solution was tested under a 320 nm exciting light and a 405 nm radiation light by an enzyme immunoassay instrument. In the experiment, water and doxycycline were used to replace the *Flemingia macrophylla* extract as the control group and the positive control group, respectively, and collagenase and the fluorogenic substrate were replaced by distilled water for determining the background value. After the tests were independently carried out three times, the mean value and standard deviation were calculated with the following formula. The results are shown in Table 2 and FIG. 7.

$$\text{Inhibition Rate (\%)} = \left[\frac{\text{Absorption value of the control group} - \text{Absorption value of the experiment group}}{\text{Absorption value of the control group}}\right] \times 100$$

TABLE 2

| Group | Extract (10 μg/mL) | Extract (50 μg/mL) | Extract (100 μg/mL) | Extract (500 μg/mL) |
|---|---|---|---|---|
| Inhibition Rate (%) | 2.4 ± 1.6 | 63.3 ± 2.6 | 66.7 ± 3.7 | 82.7 ± 2.2 |

Figure 7:
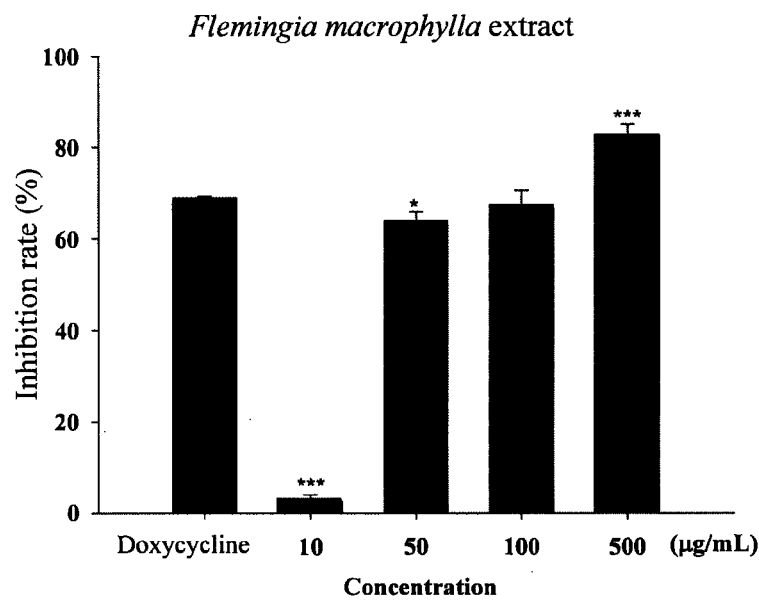
FIG. 7 is a bar diagram showing the inhibition rate of the *Flemingia macrophylla* extract of the present invention on collagenase.

As shown in Table 2 and FIG. 7, the inhibition effect of the *Flemingia macrophylla* extract was concentration-dependent and it had an excellent inhibition effect on collagenase.

Example 2

Experiment C

Inhibition Test of Matrix Metalloproteinase Expression

A total of 5×10$^5$ fibroblast Hs68 (human foreskin fibroblast, Bioresource Collection and Research Center (BCRC) number: 60038, purchased from Food Industry Research and Development Institute (FIRDI)) was counted and cultivated in a culture medium (90% Dulbecco's modified Eagle's medium adjusted with 4 mM of L-glutamine, containing 1.5 g/L NaHCO$_3$, 4.5 g/L glucose, and 10% fetal bovine serum) with a diameter of 10 cm. After the fibroblast Hs68 grew to a density of 80%, the culture solution was removed, and the cells were rinsed with 5 mL of a phosphate buffer saline (PBS) solution once. Then, 3 mL of a phenol red-free culture solution containing the *Flemingia macrophylla* extract with different concentrations (0 to 50 μg/mL) was added into the culture medium, and was reacted for 1 hour. The cells were placed under ultraviolet light (80 mJ/cm$^2$, Ultraviolet B (UVB)) for irradiation. Afterwards, 7 mL of a phenol red-free culture solution containing the *Flemingia macrophylla* extract with different concentrations (0 to 50 μg/mL) was further added into the culture medium, and the cells were cultured in an incubator at 37° C. containing 5 vol % carbon dioxide for 48 hours, and then the cells were collected.

A lysing buffer solution (comprising 100 mM Na$_3$VO$_4$, 100 mg/mL Phenylmethanesulfonyl fluoride (PMSFL), 20 mg/mL Leupeptin, 50 mM Tris-HCl with pH 7.4, 37.5 mM NaCl, 250 mM DL-dithiothreitol, 3 mM of sodium deoxycholate, 1 mM EDTA, 0.1% SDS, and 1% Igepal™ CA-630 (purchased from Sigma-Aldrich)) was used to treat the collected cells. An additional physical vibration was applied to break the cell membranes, and the cell organelles and fragments were precipitated by a centrifuge. The supernatant containing cytoplasm proteins was collected. Then, the collected proteins were separated by SDS-PAGE gel electrophoresis and were transferred to a membrane by western blotting. Based on the antigen-antibody principle, antibodies were used to detect target proteins, including Type I procollagen, MMP-1, MMP-3, MMP-9, and β-actin. Using luminescence imaging technology with an associated analysis software and LAS-4000 (FUJIFILM) to record the image, a quantitative analysis was carried out by a multi Gauge V2.2 (Steware Technology Inc.) to test the variation of the expression of target proteins.

Figure 8:
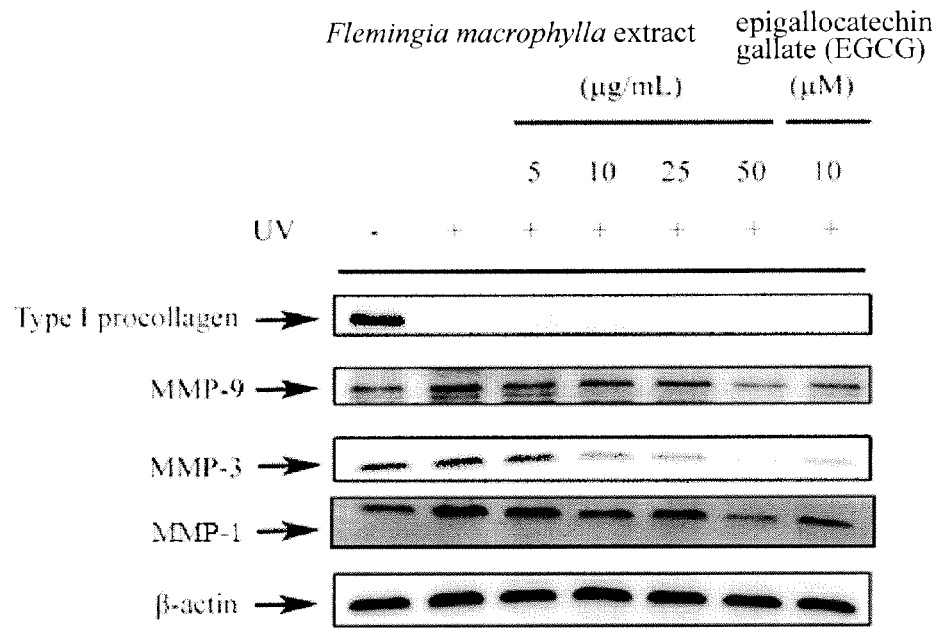
FIG. 8 is a protein electrophoresis picture of matrix metalloproteinase (MMP-1, MMP-3, and MMP-9) and Type I pro-collagen in fibroblast Hs68.
Figure 9:
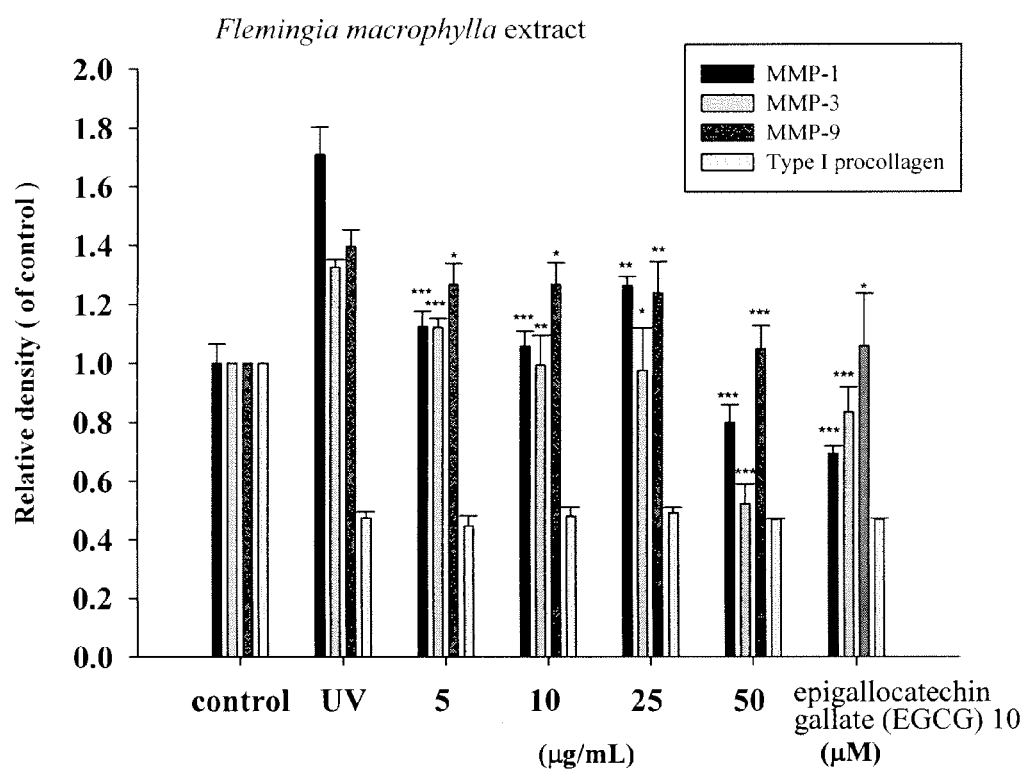
FIG. 9 is a bar diagram showing the inhibition rate of the *Flemingia macrophylla* extract of the present invention on matrix metalloproteinase (MMP-1, MMP-3, and MMP-9)

As shown in FIG. 8 and FIG. 9, after UV light radiation, the expression amount of MMP 1, MMP-3, and MMP-9 in the fibroblasts increased to 1.7-fold, 1.3-fold, and 1.4-fold, respectively. The expression of collagen was decreased. After UV light radiation, the fibroblasts were further treated by the *Flemingia macrophylla* extract, and in the concentration of 10 μg/mL of the extract, the expression of MMP-1 decreased significantly from 1.7-fold to 1.0-fold; the expression of MMP-3 decreased from 1.3-fold to 0.9-fold; and the expression of MMP-9 decreased from 1.4-fold to 1.2-fold.

The test result showed that the *Flemingia macrophylla* extract can inhibit the expression of matrix metalloproteinase.

Example 3

Experiment D

Inhibition Test of Mitogen-Activated Protein Kinase Phosphorylation

First, the fibroblast (human foreskin fibroblast, Bioresource Collection and Research Center (BCRC) number: 60038, purchased from Food Industry Research and Development Institute (FIRDI)) was cultivated in a culture medium (90% Dulbecco's modified Eagle's medium adjusted with 4 mM of L-glutamine, containing 1.5 g/L NaHCO$_3$, 4.5 g/L glucose, and 10% fetal bovine serum). After the fibroblast grew to a density of 80%, the culture solution was changed and cultivated in the culture solution containing different concentrations of the *Flemingia macrophylla* stem extract (5 to 50 μg/mL, dissolved in DMSO) for 15 mins. Then, the culture solution was removed and the fibroblast cells were rinsed twice with the PBS solution. The PBS solution was then added into the culture medium. After the cells were irradiated under ultraviolet light (40 mJ/cm$^2$, Ultraviolet B (UVB)), the PBS solution was removed, and then a culture solution comprising no serum was added to culture the fibroblast cells. The proteins within the fibroblast cells were isolated after 24 hours, and the expression of unphosphorylated and phosphorylated mitogen-activated protein kinases (JNK, ERK, and p38 protein) within the fibroblast cells were observed by the Western-blotting method.

After the fibroblast cells were irradiated with short wavelength UV the mitogen-activated protein kinase (MAP Kinase) was induced to undergo phosphorylation, and the MAP Kinase pathway was activated, therefore triggering the photo-aging.

Figure 10:
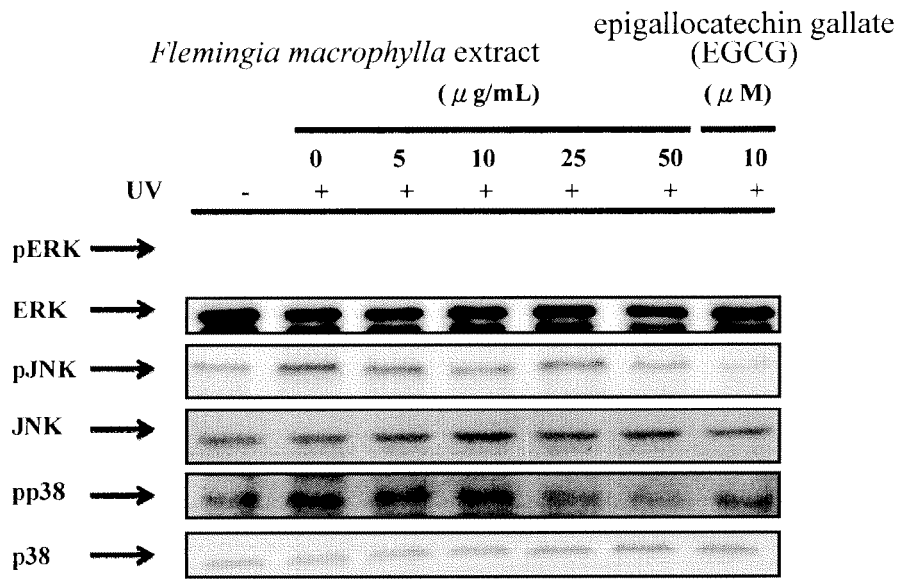
FIG. 10 is a protein electrophoresis picture of unphosphorylated and phosphorylated mitogen-activated protein kinase (JNK, ERK, and p38 protein) in fibroflast Hs68.
Figure 11:
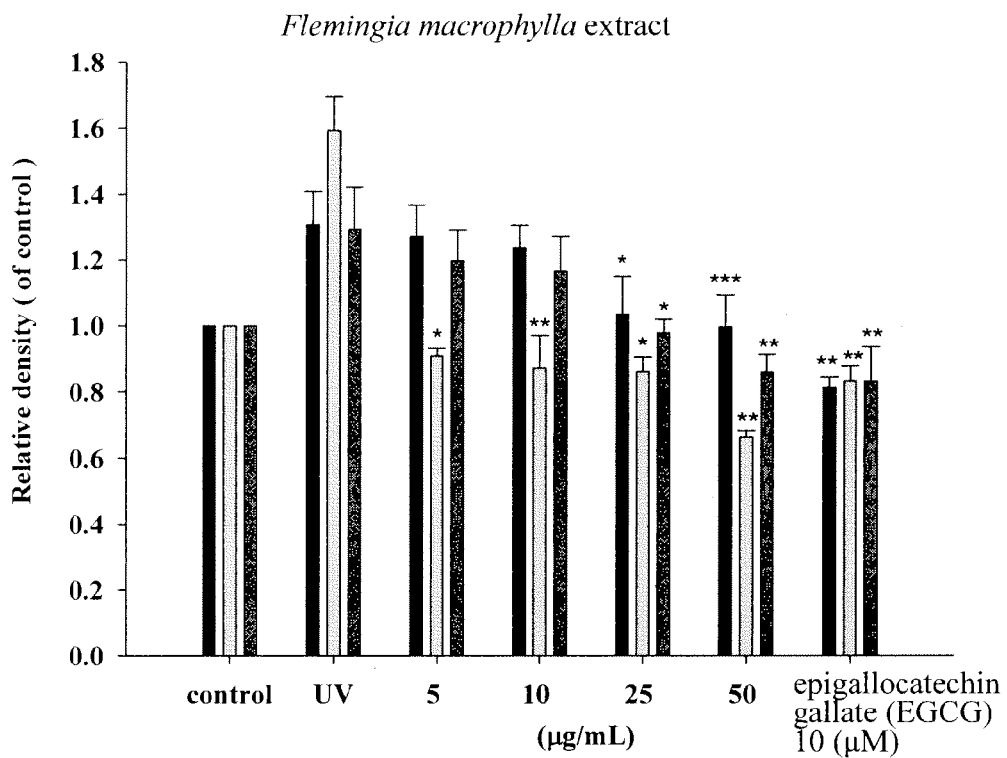
FIG. 11 is a bar diagram showing the inhibition of the *Flemingia macrophylla* extract of the present invention on the phosphorylatation of mitogen-activated protein kinase (JNK, ERK, and p38 protein)

As shown in FIG. 10 and FIG. 11, after the fibroblast cells were irradiated by short wavelength UV, the expression amount of phosphorylated ERK, JNK, and p38 was 1.3, 1.6, and 1.3-fold compared to the non-irradiated control group. After being treated with the *Flemingia macrophylla* stem extract, the phosphorylation of ERK can be inhibited in the concentration of 25 μg/mL, and the phosphorylation decreased from 1.3-fold to 1-fold. The phosphorylation of JNK decreased from 1.6-fold to 0.9-fold in the concentration of 5 μg/mL, and the phosphorylation of p38 decreased from 1.3-fold to 1-fold in the concentration of 25 μg/mL.

This example illustrates that the *Flemingia macrophylla* extract of the present invention can effectively inhibit the phosphorylation of mitogen-activated protein kinase, and therefore can inhibit photo-aging.

Example 4

Experiment E

Anti-Oxidation Tests—DPPH Free Radicals Removal Test

DPPH (1,1-diphenyl-2-picrylhydrazyl) was used as the source of free radicals to test the ability of the *Flemingia macrophylla* extract to remove free radicals. A 100 μL of the *Flemingia macrophylla* extract with different concentrations (0.05 to 5 μg/mL) and a 100 μL DPPH solution (200 μM) dissolved in water were added in a 96-well microplate, and were mixed evenly and placed under room temperature away from light for 30 minutes. The absorbance of the mixture was determined by an enzyme immunoassay instrument with a wavelength of 517 nm. In this test, the extract was replaced by 50 vol % propylene glycol as the control group, and vitamin C was used as a positive control group, and DPPH was replaced by methanol for determining the background value. The ability of the *Flemingia macrophylla* extract to remove free radicals was calculated by the following formula. The results are shown in Table 3 and FIG. 12.

$$\text{Scavenge efficiency}(\%) = \left[ \frac{(\text{Absorption value of the control group}) - (\text{Absorption value of the experiment group})}{\text{Absorption value of the control group}} \right] \times 100$$

TABLE 3

| | concentration (μg/mL) *Flemingia macrophylla* extract | | | |
|---|---|---|---|---|
| | 0.25 | 0.5 | 2.5 | 5 |
| scavenge efficiency (%) | 12.6 ± 1.6 | 31.4 ± 0.3 | 62.8 ± 1.1 | 92.9 ± 1.4 |

Figure 12:
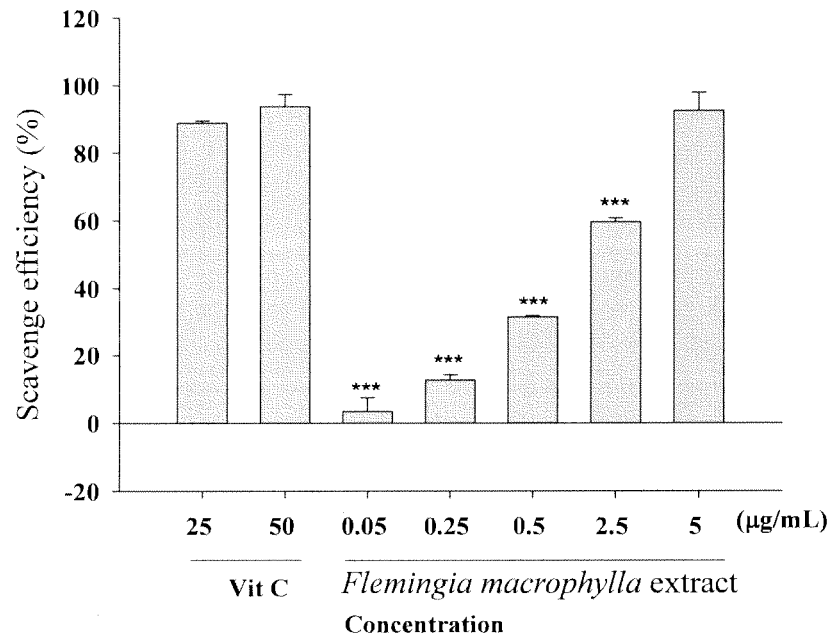
FIG. 12 is a bar diagram showing the scavenging rate of the *Flemingia macrophylla* extract of the present invention on DPPH free radicals.

As shown in Table 3 and FIG. 12, the ability (scavenge efficiency) of the *Flemingia macrophylla* extract with different concentrations (0.25, 0.5, 2.5, and 5 μg/mL) to remove DPPH free radicals is 12.6±1.6%, 31.4±0.3%, 62.8±1.1%, and 92.9±1.4%, respectively, and in the concentration of 5 μg/mL, the extract has comparative scanvenge effect as vitamin C.

The test result showed that the *Flemingia macrophylla* extract can effectively remove DPPH free radicals, thus it has excellent anti-oxidation effect.

Experiment F

Anti-oxidation Tests—AAPH Free Radicals Inhibition Test

AAPH (2,2'-Azobis(2-methylpropionamidine)dihydrochloride) was used as the free radical source, and rat red blood cells were used to mimic a biomembrane to examine the ability of the *Flemingia macrophylla* extract to protect biomembrane from the damage of free radicals. First, a moderate amount of rat blood was placed into the eppendorf tube comprising heparin, and the PBS was added and mixed evenly. The samples were centrifuged at 3000 g for 15 minutes and the supernatants were removed. After the procedure was repeated for 5 times, 4 times the weight of PBS was added to the sample to form a 20% red blood cell suspension.

Figure 13A:
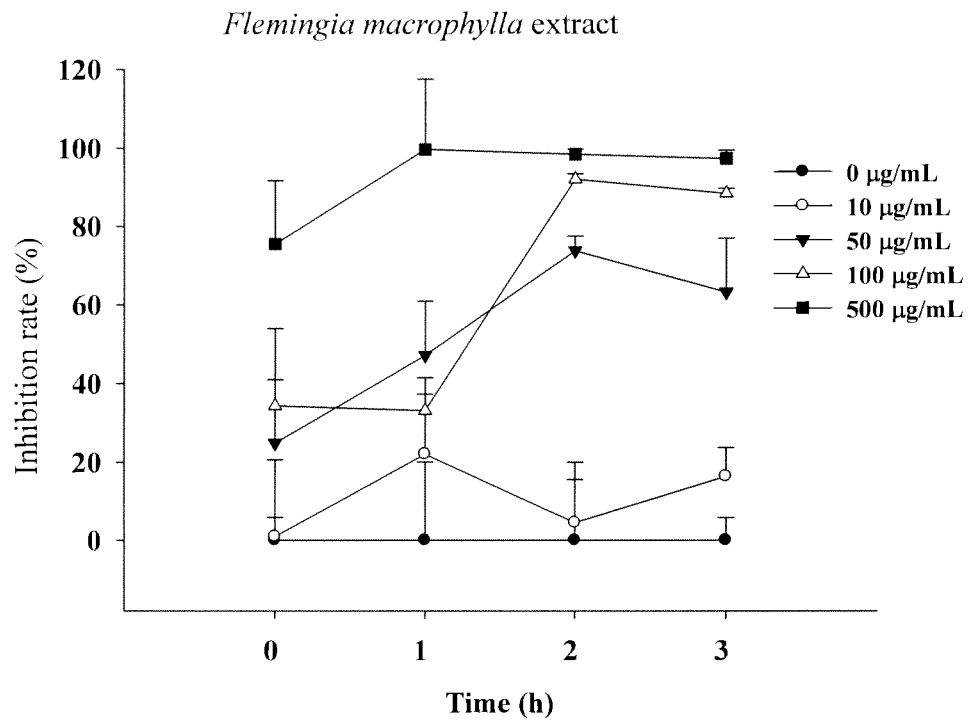
FIGS. 13A and 13B are curve diagrams showing the inhibition rate of the *Flemingia macrophylla* extract of the present invention on AAPH free radicals.
Figure 13B:
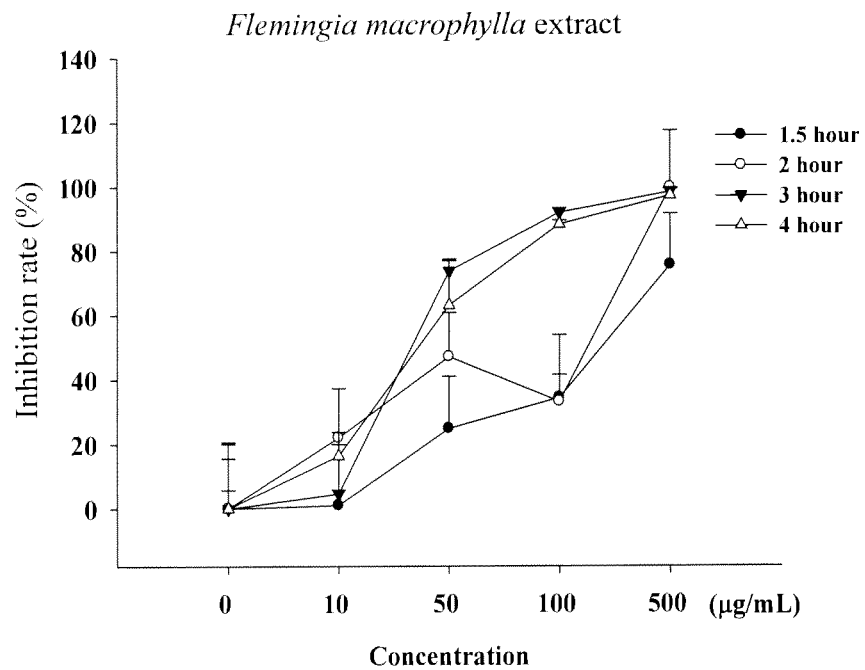

In an eppendorf tube, a 100 μL of the *Flemingia macrophylla* extract with different concentrations (0 to 500 μg/mL) was added into a solution containing 100 μL of the 20% red blood cell suspension and a 100 μL of an AAPH solution (300 mM), and mixed gently with a vibrator and reacted under 37° C. The samples were taken at a reaction time of 0, 1, 1.5, 2, 3, and 4 hours (number of sample=3), and 300 μL of a phosphate buffer solution was added therein to terminate the reaction. Then, the samples were centrifuged at 3000 g for 2 minutes. The supernatant (200 μL) was collected and placed in a 96-well microplate, and the absorbance thereof was tested by an enzyme immunoassay instrument with a wavelength of 540 nm. The extract was replaced by the PBS as the control group, and the 20% red blood cell suspension was replaced by the PBS to determine the background value. The ability of the *Flemingia macrophylla* extract to inhibit free radicals was calculated by the following formula. The results are shown in FIG. 13A and FIG. 13B.

$$\text{Inhibition Rate (\%)} = \left[\frac{\text{Absorption value of the control group} - \text{Absorption value of the experiment group}}{\text{Absorption value of the control group}}\right] \times 100$$

The results showed that the samples not treated by AAPH did not show hemolysis during the reaction (1, 2, 3, and 4 hours), but after the samples were treated by AAPH and reacted under 37° C. for 2 hours, hemolysis was observed. The degree of hemolysis was higher with the increase of the reaction time, indicating that the hemolysis of red blood cells induced by AAPH was time-dependent. FIGS. 13A and 13B show that when the samples were treated by the PBS that contained different concentrations of the *Flemingia macrophylla* extract, in the concentration of 50 µg/mL, the extract showed significant inhibition effect on the hemolysis induced by AAPH free radicals after 3 hours. The inhibition rate of the extract was 73.7±3.7%. In addition, the inhibition rate increased (88.4±1.0 to 95.0±3.3%) with the increase of the concentration of the *Flemingia macrophylla* extract (100 to 500 µg/mL), indicating that the anti-free radical effect of the *Flemingia macrophylla* extract was concentration-dependent.

This test shows that the *Flemingia macrophylla* extract can effectively inhibit the activity of free radicals, and thus has excellent anti-oxidation ability.

Experiment G

Anti-Oxidation Tests—$H_2O_2$ Clearance Test

Hydrogen peroxide ($H_2O_2$) can rapidly penetrate a cell membrane and react with $Fe^{2+}$ or $Cu^{2+}$ ions to form hydroxyl radicals in the cells. Hydroxyl radical is the most reactive and aggressive free radical, and it can rapidly react with any molecules in the body to cause damage, and denature some enzymes by oxidizing the sulfhydryl group thereon. The absorbance values in this test were measured by using an enzyme immunoassay instrument with a wavelength of 230 nm. Vitamin C was used as a positive control group to observe the scavenging ability of the *Flemingia macrophylla* extract on hydrogen peroxide. The results are shown in Table 4 and FIG. 14.

TABLE 4

| | concentration (µg/mL) *Flemingia macrophylla* extract | | | | |
|---|---|---|---|---|---|
| | 5 | 10 | 50 | 100 | 500 |
| scavenge efficiency (%) | 0.2 ± 4.7 | 2.1 ± 5.3 | 11.2 ± 1.8 | 69.6 ± 3.0 | 107.7 ± 2.1 |

Figure 14:
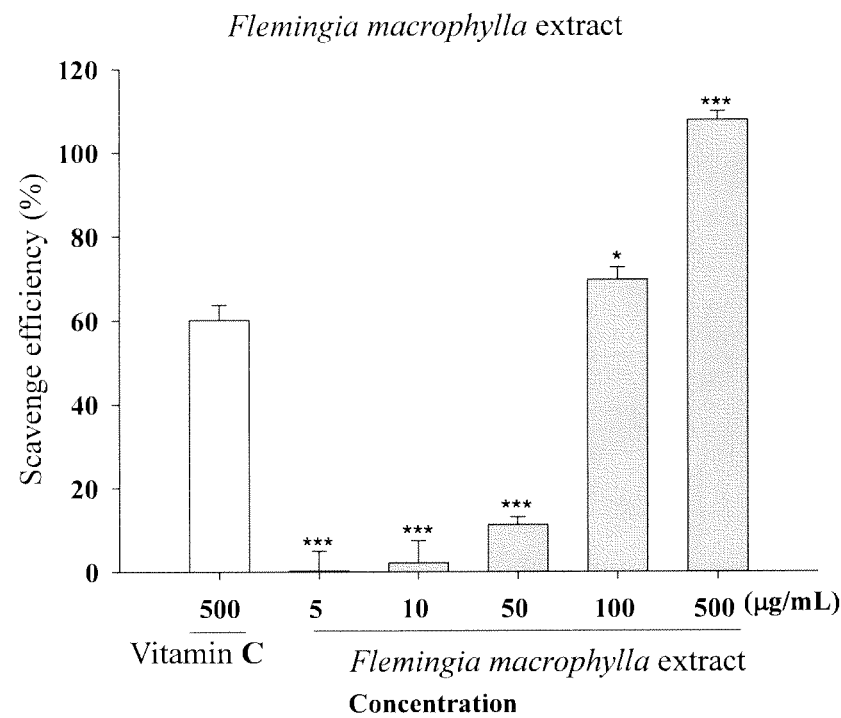
FIG. 14 is a bar diagram showing the scavenging rate of the *Flemingia macrophylla* extract of the present invention on $H_2O_2$.

As shown in Table 4 and FIG. 14, the scavenge efficiency of the *Flemingia macrophylla* extract on hydrogen peroxide was increased with the increase of the concentration of the extract, indicating that the ability of the *Flemingia macrophylla* extract to eliminate hydrogen peroxide was concentration-dependent, and that the extract had excellent anti-oxidation activity.

Experiment H

Anti-Oxidation Tests—Ferrous Ions Chelation Test

The pro-oxidation of metal ions is usually the major cause for lipid oxidation, and lipid oxidation can be accelerated by free radicals generated by only a small amount of metal ions via reduction-oxidation. Ferrous ions ($Fe^{2+}$) have the highest pro-oxidative activity, and thus, if $Fe^{2+}$ can be efficiently chelated, the Fenton reaction can be prevented. Accordingly, $Fe^{2+}$ chelation can be one of the evaluation items for assessing anti-free radical ability. The absorbance values in this test were measured by an enzyme immunoassay instrument with a wavelength of 562 nm. Ethylenediaminetetraacetic acid (EDTA) was used as a positive control group to observe the chelating effect of the *Flemingia macrophylla* extract on $Fe^{2+}$. The results are shown in Table 5 and FIG. 15.

TABLE 5

| | concentration (µg/mL) *Flemingia macrophylla* extract | | | | |
|---|---|---|---|---|---|
| | 5 | 10 | 50 | 100 | 500 |
| chelating efficiency (%) | 2.9 ± 5.8 | 1.6 ± 3.7 | 6.0 ± 3.6 | 6.9 ± 2.7 | 28.7 ± 1.9 |

Figure 15:
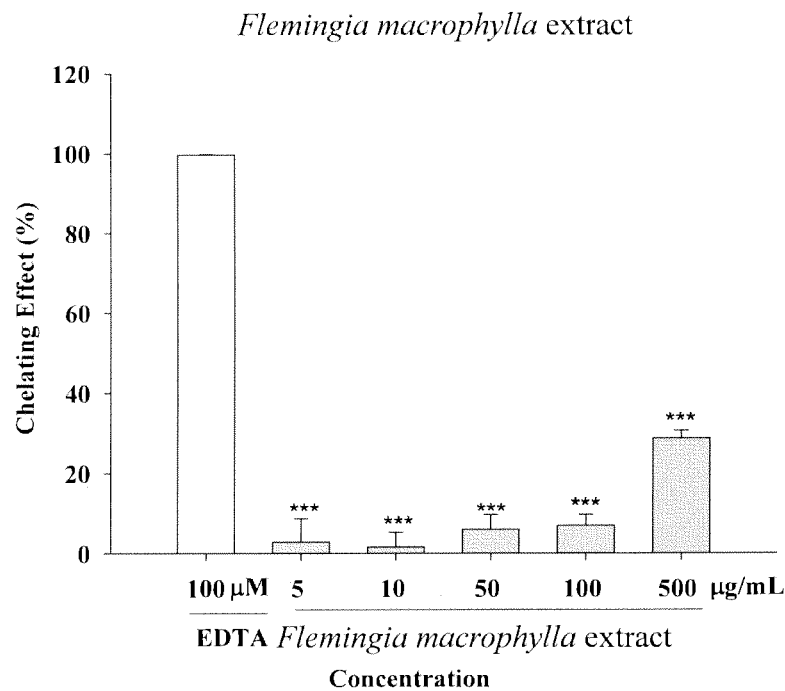
FIG. 15 is a bar diagram showing the chelating effect of the *Flemingia macrophylla* extract of the present invention on ferrous ions.

As shown in Table 5 and FIG. 15, the chelating effect of the *Flemingia macrophylla* extract with $Fe^{2+}$ increased with the increase of the concentration of the *Flemingia macrophylla* extract, indicating that the *Flemingia macrophylla* extract can achieve the anti-oxidation effect by chelating with $Fe^{2+}$.

Example 5

Experiment I

Cytotoxicity Test

The cytotoxicity of the *Flemingia macrophylla* extract was observed with the MTT (3-(4,5-dimethylthiazol-2-yl)-2,5-diphenyl tetrazolium bromide) assay. First, 50 µL of various concentrations (0 to 200 µg/mL) of the *Flemingia macrophylla* extract was added into a 96-well culture plate that comprised fibroblast Hs68 ($10^4$ cells/well). After the cells were incubated in an incubator comprising 5 vol % carbon dioxide at 37° C. for 24 hours, 15 µL of a MTT solution (5 mg/mL, in PBS) was added into the well, and the fibroblasts were further incubated for 3 hours. Then, 75 µL of a sodium dodecyl sulfate (SDS) solution (10% SDS, in 0.01N HCl) was added into the culture plate, and the absorbance of each well was measured by an enzyme immunoassay instrument with a wavelength of 570 nm after 24 hours. Finally, the cell survival rate was calculated by the following formula, and the cytotoxicity of the extract was observed. The results are shown in Table 6 and FIG. 16.

$$\text{Cellular Survival Rate (\%)} = \left[\frac{\text{Absorption value of the experiment group}}{\text{Absorption value of the control group}}\right] \times 100$$

TABLE 6

| | Concentration of the extract (µg/mL) | | | | | |
|---|---|---|---|---|---|---|
| | 0 | 5 | 10 | 50 | 100 | 200 |
| Cellular Survival Rate (100%) | 100 ± 8.2 | 107.2 ± 7.6 | 110.7 ± 7.9 | 100.8 ± 11.9 | 103.3 ± 5.4 | 87.5 ± 2.3* |

(*P < 0.05)

Figure 16:
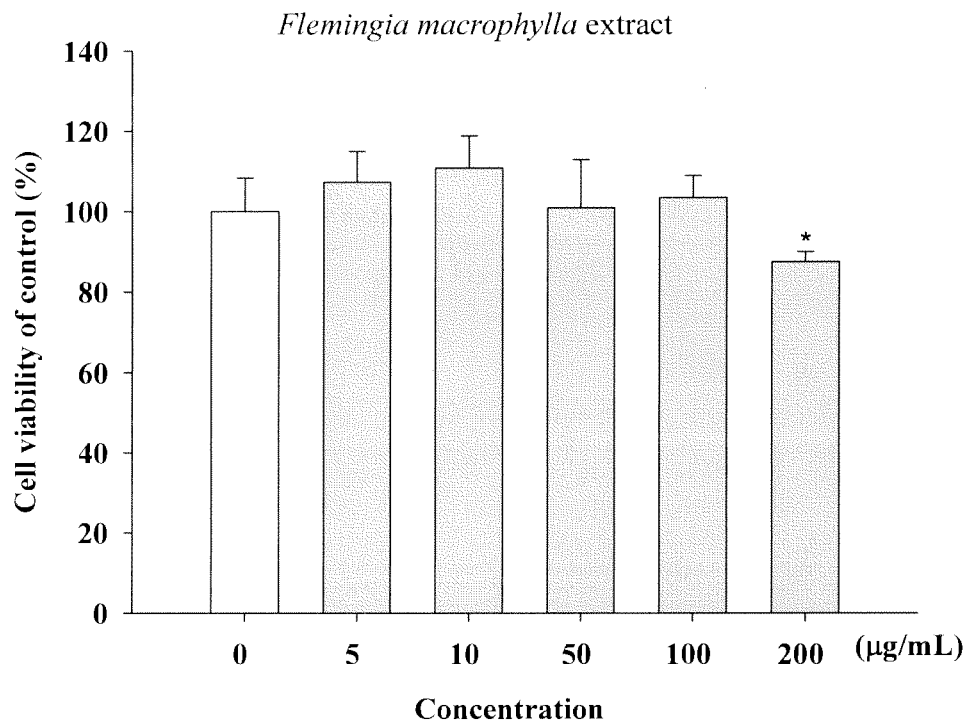
FIG. 16 is a bar diagram showing the cell viability of fibroblast Hs68.

As shown in Table 6 and FIG. 16, after the fibroblasts were treated by the *Flemingia macrophylla* extract at the concentration of 1 to 200 μg/mL, even at the high dosage of 200 μg/mL, the extract showed no cytotoxicity to the fibroblasts. When the concentration was higher than 5 μg/mL, the extract showed a cellular proliferation effect.

According to the above tests, the *Flemingia macrophylla* extract of the present invention has excellent effects of antioxidation, inhibiting the activity of matrix metalloproteinase, inhibiting the expression of matrix metalloproteinase, and/or inhibiting the phosphorylation of mitogen-activated protein kinase, and it is non-toxic. Therefore, the extract can achieve the effects of improving, repairing, and/or caring for skin without injuring the human body or animal.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A method of inhibiting at least one selected from the group consisting of oxidation, the activity of matrix metalloproteinase (MMP), the expression of matrix metalloproteinase, and the phosphorylation of mitogen-activated protein kinase (MAP kinase) in a mammal, in need thereof comprising administering to the mammal an effective amount of a *Flemingia macrophylla* stem extract; wherein the extract is administered in an amount effective to improve skin, repair skin, care for skin, and/or inhibit photoaging.

2. The method as claimed in claim 1, wherein the extract has a first absorption peak at a wavelength ranging from 255 to 290 nm.

3. The method as claimed in claim 2, wherein the first absorption peak is at a wavelength ranging from 255 to 280 nm.

4. The method as claimed in claim 2, wherein the extract further has a second absorption peak at a wavelength ranging from 210 to 250 nm.

5. The method as claimed in claim 3, wherein the extract further has a second absorption peak at a wavelength ranging from 215 to 245 nm.

6. The method as claimed in claim 1, wherein the extract has a first absorption peak at a wavelength ranging from 255 to 280 nm and the extract is prepared by the following steps:

a) extracting *Flemingia macrophylla* stem with a solvent and collecting the liquid phase; and b) drying the collected liquid phase optionally, wherein the solvent is selected from a group consisting of water, alcohols, and combinations thereof.

7. The method as claimed in claim 6, wherein the solvent is selected from a group consisting of water, $C_1$-$C_4$ alcohols, and combinations thereof.

8. The method as claimed in claim 6, wherein the solvent is selected from a group consisting of water, methanol, ethanol, propanol, butanol, propylene glycol, and combinations thereof.

9. The method as claimed in claim 6, wherein the solvent is selected from a group consisting of water, methanol, and a combination thereof.

10. The method as claimed in claim 6, wherein the matrix metalloproteinase is selected from a group consisting of matrix metalloproteinase-1 (MMP-1), matrix metalloproteinase-3 (MMP-3), matrix metalloproteinase-9 (MMP-9), and combinations thereof.

11. The method as claimed in claim 6, wherein the mitogen-activated protein kinase is selected from a group consisting of c-Jun N-terminal Kinase (JNK), extracellular signal-regulated protein kinase (ERK), p38 protein, and combinations thereof.

12. The method as claimed in claim 6, wherein the extract is administered in an amount effective to inhibit photoaging induced by ultraviolet ray B (UVB).

13. The method as claimed in claim 6, wherein the extract is administered as a medicament.

14. The method as claimed in claim 1, wherein the matrix metalloproteinase is selected from a group consisting of matrix metalloproteinase-1 (MMP-1), matrix metalloproteinase-3 (MMP-3), matrix metalloproteinase-9 (MMP-9), and combinations thereof.

15. The method as claimed in claim 1, wherein the mitogen-activated protein kinase is selected from a group consisting of c-Jun N-terminal Kinase (JNK), extracellular signal-regulated protein kinase (ERK), p38 protein, and combinations thereof.

16. The method as claimed in claim 1, wherein the extract is administered in an amount effective to improve skin, repair skin, and/or care for skin.

17. The method as claimed in claim 1, wherein the extract is administered as a medicament.

* * * * *